United States Patent
House et al.

(10) Patent No.: US 9,095,277 B2
(45) Date of Patent: Aug. 4, 2015

(54) DELIVERY CATHETER WITH FORWARD-LOOKING ULTRASOUND IMAGING

(75) Inventors: Morgan House, Newfields, NH (US); Steven Cahalane, Pelham, NH (US)

(73) Assignee: MITRALIGN, INC., Tewksbury, MA (US)

( * ) Notice: Subject to any disclaimer, the term of this patent is extended or adjusted under 35 U.S.C. 154(b) by 266 days.

(21) Appl. No.: 13/158,012

(22) Filed: Jun. 10, 2011

(65) Prior Publication Data
US 2012/0089022 A1 Apr. 12, 2012

Related U.S. Application Data

(60) Provisional application No. 61/363,153, filed on Jul. 9, 2010.

(51) Int. Cl.
*A61B 8/12* (2006.01)
*A61B 8/08* (2006.01)
*A61B 8/00* (2006.01)

(52) U.S. Cl.
CPC .................. *A61B 8/0883* (2013.01); *A61B 8/12* (2013.01); *A61B 8/445* (2013.01); *A61B 8/0891* (2013.01)

(58) Field of Classification Search
USPC .......................................... 600/407, 437–472
See application file for complete search history.

(56) References Cited

U.S. PATENT DOCUMENTS

| | | | |
|---|---|---|---|
| 2005/0256410 A1* | 11/2005 | Rabiner et al. | 600/470 |
| 2008/0255447 A1* | 10/2008 | Bourang et al. | 600/434 |
| 2009/0088631 A1* | 4/2009 | Dietz et al. | 600/424 |

* cited by examiner

*Primary Examiner* — Mark Remaly
(74) *Attorney, Agent, or Firm* — Leason Ellis LLP

(57) ABSTRACT

A catheter based medical device is provided for a percutaneous surgical procedure that provides forward-looking visualization and delivery of a medical device. The catheter includes a carriage at its distal end and an ultrasonic transducer is supported by the carriage. A conduit that has its proximal end disposed within the catheter and the conduit passes through the sidewall of the catheter proximate to the distal end of the catheter so that the distal end of the conduit is disposed on an exterior of the sidewall of the catheter. A medical device is deliverable through the lumen of the conduit and the ultrasonic transducer provides visualization of the medical device distally of the transducer.

15 Claims, 9 Drawing Sheets

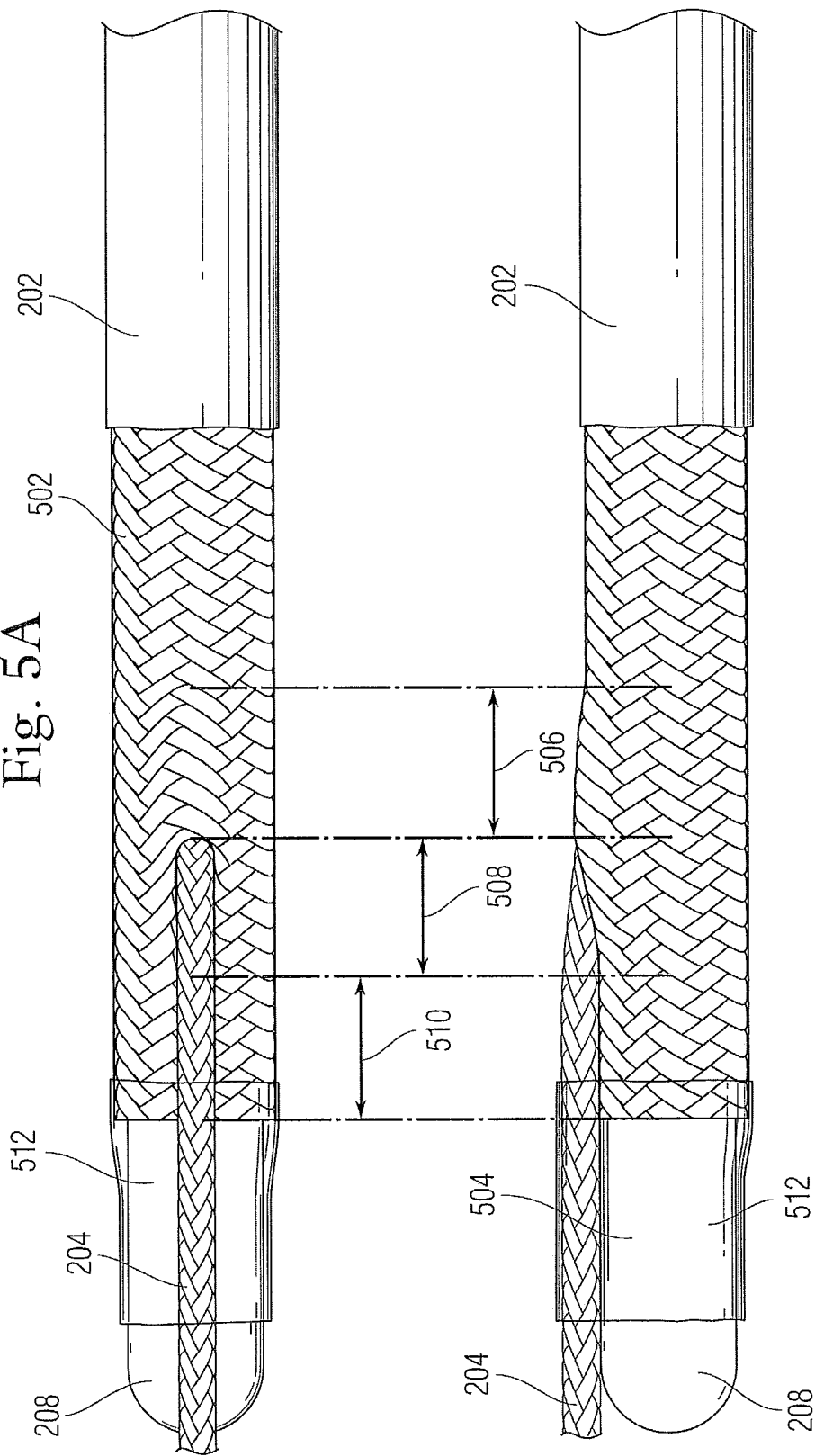

DELIVERY CATHETER WITH FORWARD-LOOKING ULTRASOUND IMAGING

CROSS-REFERENCE TO RELATED APPLICATIONS

The present application claims the benefit of U.S. patent application Ser. No. 61/363,153, filed Jul. 9, 2010, which is hereby incorporated by reference in its entirety.

FIELD OF THE INVENTION

The invention relates to catheters providing forward-looking imaging and more specifically relates to catheters configured to provide forward-looking ultrasound imaging in combination with a portal adapted for forward-delivery of medical devices and/or other therapeutic agent(s)

BACKGROUND OF THE INVENTION

Percutaneous catheter based surgery is known for performing procedures on various tissues/organs within the body. Traditionally, during a procedure, clinicians rely on X-ray fluoroscopic images that comprise plane-view images showing the external shape of the silhouette of the lumen or cavity in the body/organ. Percutaneous catheter- and to provide intra-operative feedback. For example, in one particular procedure, the precise placement and desired expansion of stents can be improved as a result of simultaneous catheter-based imaging. Conventional intravascular imaging devices are large and not sufficiently flexible to be placed simultaneously with other devices.

In order to resolve these issues, an ultrasonic transducer device has been utilized for endovascular intervention to visualize the inside of the blood vessels. Certain current technology is based on one or more stationary ultrasound transducers or an arrangement for rotating a single transducer relative to the catheter. A problem with known devices of this type is that they are not well suited for use with other catheters, such as catheter-mounted interventional devices.

Additionally, many devices provide side-looking images which again is not well suited for providing guidance during invasive procedures. Forward-looking ultrasound imaging is essential in guiding an interventional device for treatment in a timely manner. For example, when implanting a heart pacemaker, electrical leads need to be implanted in precise locations. The present invention provides a solution that combines forward-looking imaging technology with the independent, concurrent delivery of an interventional catheter instrument.

BRIEF DESCRIPTION OF THE DRAWING FIGURES

FIG. 5A is a top view of a delivery catheter with forward-looking ultrasound imaging device according to an embodiment of the invention;

FIG. 5B is a side view of a delivery catheter with forward-looking ultrasound imaging device according to an embodiment of the invention;

DETAILED DESCRIPTION OF CERTAIN EMBODIMENTS OF THE INVENTION

Embodiments of the invention will now be described with reference to the accompanying drawing figures, wherein like numerals refer to like elements throughout. The terminology used in the description presented herein is not intended to be interpreted in any limited or restrictive manner simply because it is being utilized in conjunction with a detailed description of certain specific embodiments of the invention.

Figure 1A:
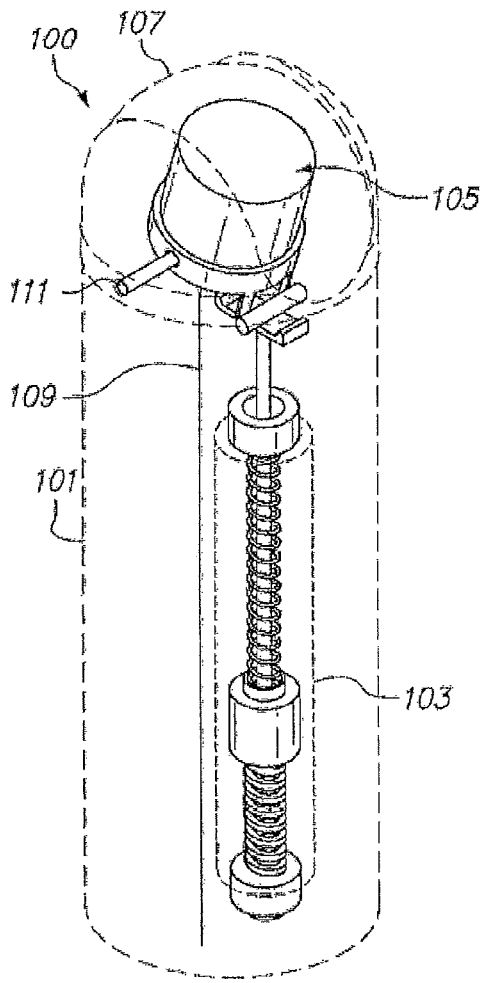
FIG. 1A is a partial cut-away perspective view of an ultrasonic transducer and actuator according to prior art.
Figure 1B:
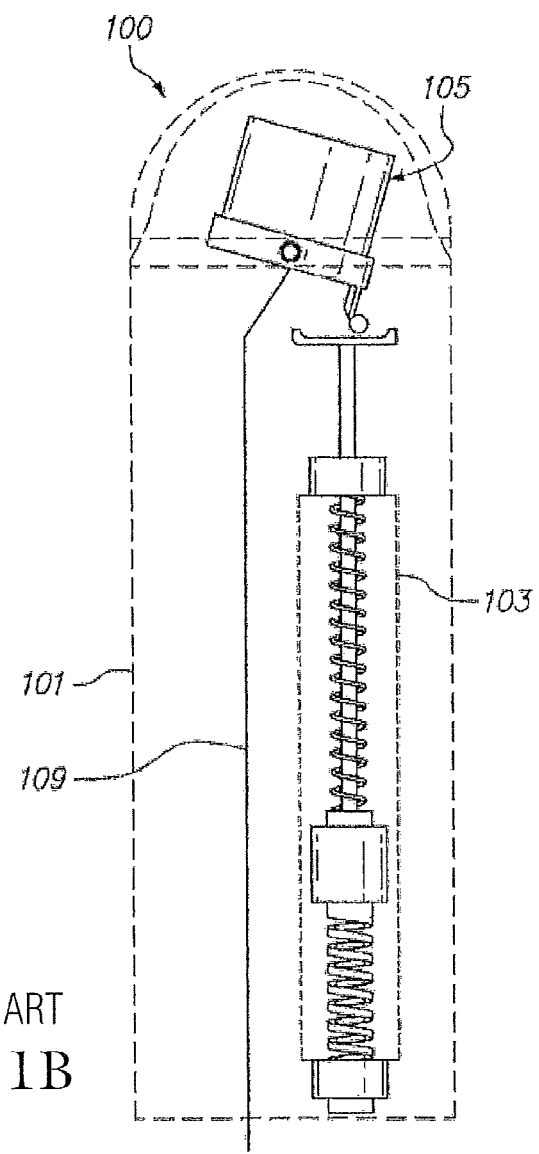
FIG. 1B is a partial cut-away side view of the ultrasonic transducer and actuator according to prior art.

FIGS. 1A and 1B illustrate an embodiment of a forward-looking intravascular ultrasound device 100 capable of sweeping or scanning forward of the distal end of the device 100 to produce ultrasound images. As shown in FIG. 1A, the device 100 includes an elongated body 101 having a distal end, a proximal end, and a longitudinal axis. The elongated body 101 is any size. In one embodiment, the elongated body 101 is small enough to fit inside a standard guide catheter with an inner diameter that is, is about, is not less than, is not less than about, is not more than, or is not more than about 12 Fr, 11 Fr, 10 Fr, 9 Fr, 8 Fr, 7 Fr, 6 Fr, 5 Fr, 4 Fr, 3 Fr, 2 Fr, 1 Fr, or falls within a range defined by, and including, any two of these values. Thus, the outside diameter of the elongated body 101 is preferably less than the inner diameter of the standard guide catheter in some embodiments.

The elongated body 101 has at least a portion 107 which is at least partially sonolucent (e.g., permits the passage of at least some ultrasound waves without absorbing or reflecting them back to their source). The portion 107 can be a window made of an ultrasound transparent material, a material which is partially or substantially transparent to ultrasound energy, or the portion 107 can be a window, opening, or aperture. In some embodiments, the entire elongated body 101 or the majority of the distal end of the elongated body 101 is formed of a substantially sonolucent material.

In some embodiments, portions of the elongate member 101 are solid and other portions, for example, the distal end, include housing portions capable of receiving other objects. Such housing portions can be tubular structures attached to the side of the distal end or attached to the distal end of the elongated body 101. Other elongated bodies 101 are tubular and have one or more lumens capable of housing other objects in the distal end. The elongated body 101 shown in FIGS. 1A and 1B houses an ultrasound transducer element 105, a local actuator 103, a coupling member 111, and an electrical wire 109. In some embodiments, the electrical wire 109 is connected to the ultrasound transducer element 105 and wrapped at least partially around the coupling member 111. In some embodiments, the transducer element 105 comprises, or is secured directly or indirectly to the coupling member 111.

The local actuator 103 is configured to engage (e.g., contact, push, or pull) the ultrasound transducer element 105 and cause the ultrasound transducer element 105 to rotate in a first direction and/or a second direction counter to the first direction about an axis of rotation. In some embodiments, the axis of rotation is generally normal to the longitudinal axis. In some embodiments, the ultrasound transducer element 105 is directly connected or coupled with the elongated body 101 and configured to rotate relative to the elongated body 101 about an axis of rotation. In some embodiments, the axis of rotation is substantially parallel to the coupling member 111. In other embodiments, the ultrasound transducer element 105 is coupled with a member 111 that extends from an interior surface of the elongated member 101 such that the ultrasound transducer element 105 rotates about the member 111.

Further details of the forward-looking intravascular ultrasound device 100 are described in detail in PCT/US2009/044218, the contents of which are incorporated herein in its entirety as if set forth herein.

Figure 2:
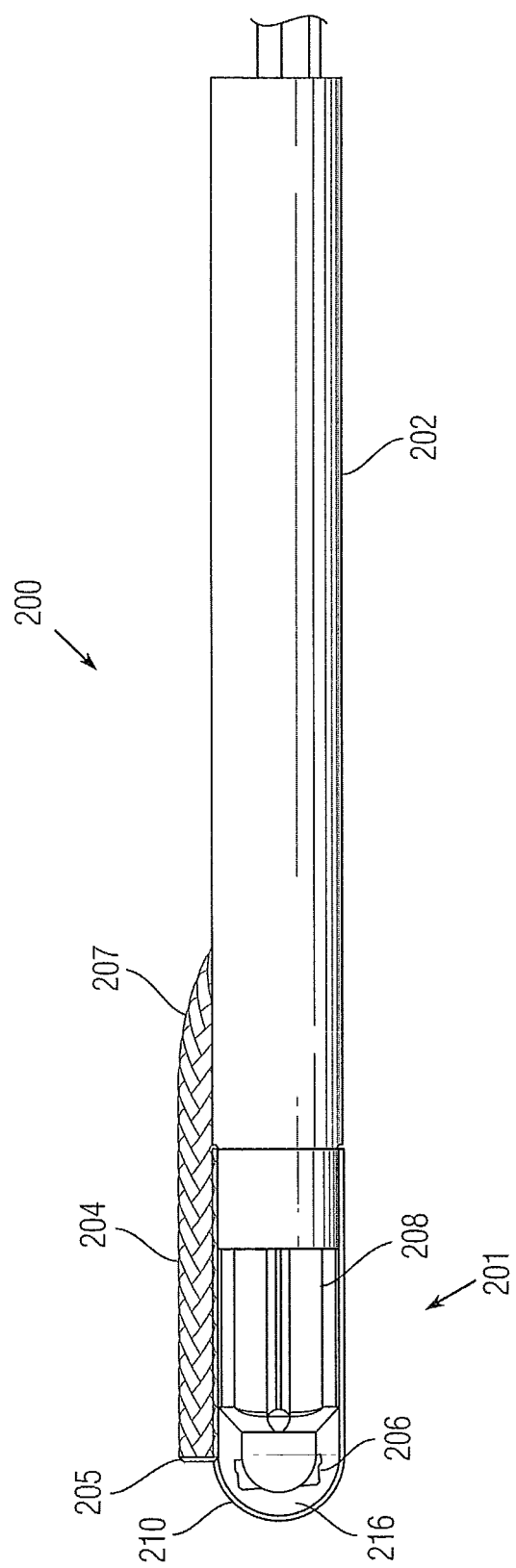
FIG. 2 is a side view of a delivery catheter with forward-looking ultrasound imaging device according to an embodiment of the invention.

Turning now to FIG. 2, this figure illustrates a medical device and or other therapeutic delivery and imaging tool 200 in accordance with an embodiment of the present invention. The tool 200 includes an elongate delivery catheter 202, an elongate medical device conduit 204, an ultrasonic transducer 206, a carriage 208 that supports the ultrasonic transducer 206, and a sonolucent acoustic window 210. The elongate delivery catheter and the elongate medical device conduit are connected to one another at least at the distal end (as shown in FIG. 2) and can be advanced as a unit into a person for forward-looking imaging while performing an intervention or diagnostic procedure using a device delivered through the elongate device conduit 204. The delivery catheter 202 and the medical device conduit 204 each have a distal end, a proximal end, and a sidewall defining an interior lumen. The transducer 206 is similar to the transducer 105 and can be actuated via an actuator 103 as shown in FIGS. 1A and 1B. The tool 200 allows for the delivery of a medical device and/or therapeutic, such as a guide wire, needle, or other intravascular medical instrument/fluid/energy, through the medical device conduit 204 and the ultrasonic transducer 206 provides forward-looking imaging of target tissue to determine the position of the medical device relative to the target tissue. Each of the components of the tool 200 are described in more detail herein.

Figure 3A:
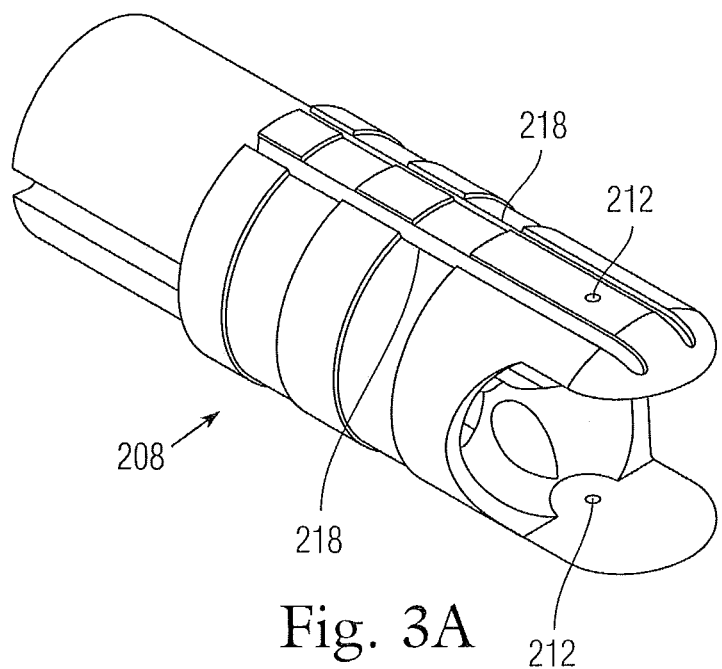
FIG. 3A is a perspective view of a ultrasonic carriage device according to an embodiment of the invention.
Figure 3B:
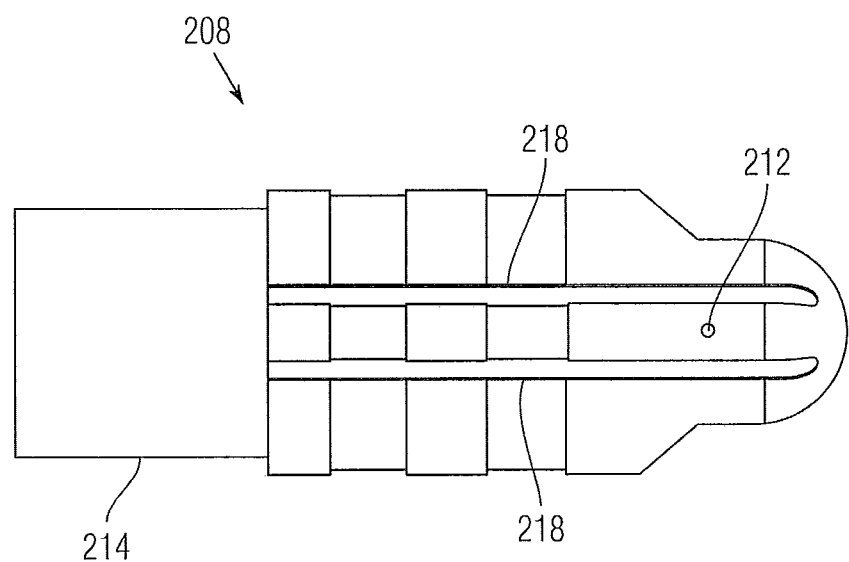
FIG. 3B is a top view of an ultrasonic carriage device according to an embodiment of the invention.

FIGS. 3A and 3B illustrate an embodiment of a carriage 208 for the ultrasonic transducer 105, 206 (omitted from FIGS. 3A and 3B for clarity). The carriage 208 includes pivot holes 212 that accept a coupling member or pin. Alternatively, the carriage walls can include pin-like protrusions or posts that are coupled with the transducer. This structural arrangement allows the transducer 206 to rotate so the transducer can move along a sweep path (e.g., 120 degrees) to facilitate ultrasonic imaging.

The carriage 208 includes a shoulder 214 that permits the carriage 208 to be mounted on the distal end of the delivery catheter 202. The delivery catheter 202 is placed over the shoulder 214 of the carriage 208 such that the carriage 208 is seated in the distal end portion of the deliver catheter 202. FIG. 2 illustrates the carriage 208 mounted on the distal end of delivery catheter 202. There are other means of coupling the carriage 208 to the distal end of the delivery catheter 202 and the use of shoulder 214 is just one example.

As shown in FIG. 2, the acoustic window 210 is placed over the carriage 208 and extends over the portion of the delivery catheter 202 that is seated on the shoulder 214 of the carriage 208. The acoustic window 210 is mounted in spaced relation to the ultrasonic transducer 206 so that the transducer 206 is capable of performing its sweeping motion free of interference by acoustic window 210. This mounting arrangement of the acoustic window 210 results in a cavity 216 between the transducer 206 and the window 210. In one embodiment, this cavity 216 is filled with saline or other fluid in order to facilitate transmission of the acoustic waves emitted from the transducer 206 through the saline in the cavity 216 and through the acoustic window 210. It is desirable to maintain a fluid environment around the transducer 206 so that the effects of any boundary conditions are minimized. The ultrasonic energy, therefore, passes through the saline, then through the sonolucent acoustic window, into a blood cavity, to tissue, and back free of any air space, in a preferred implementation.

Figure 4A:
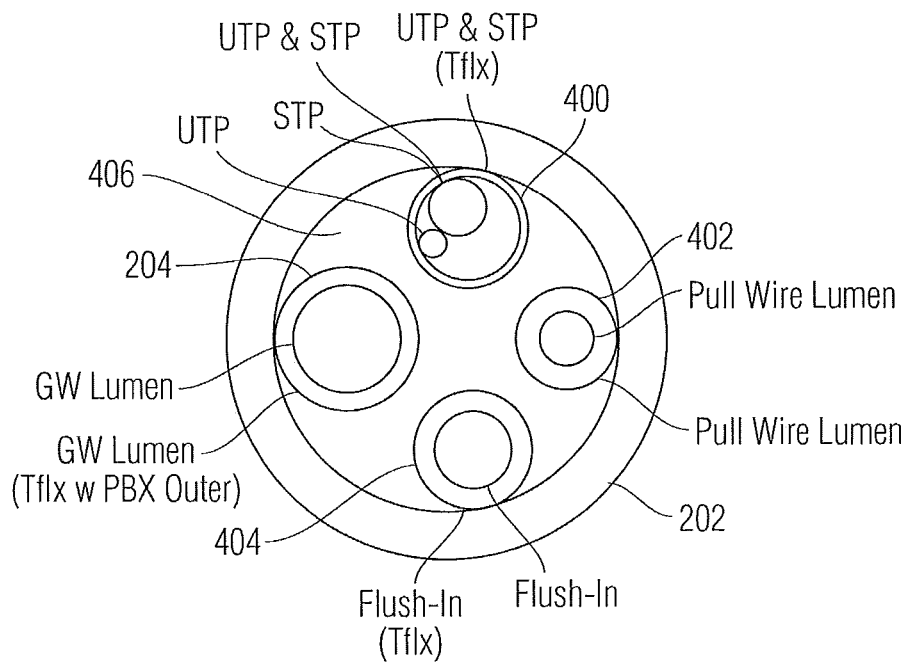
FIG. 4A is a cross-section view of the delivery catheter of FIG. 2.
Figure 4B:
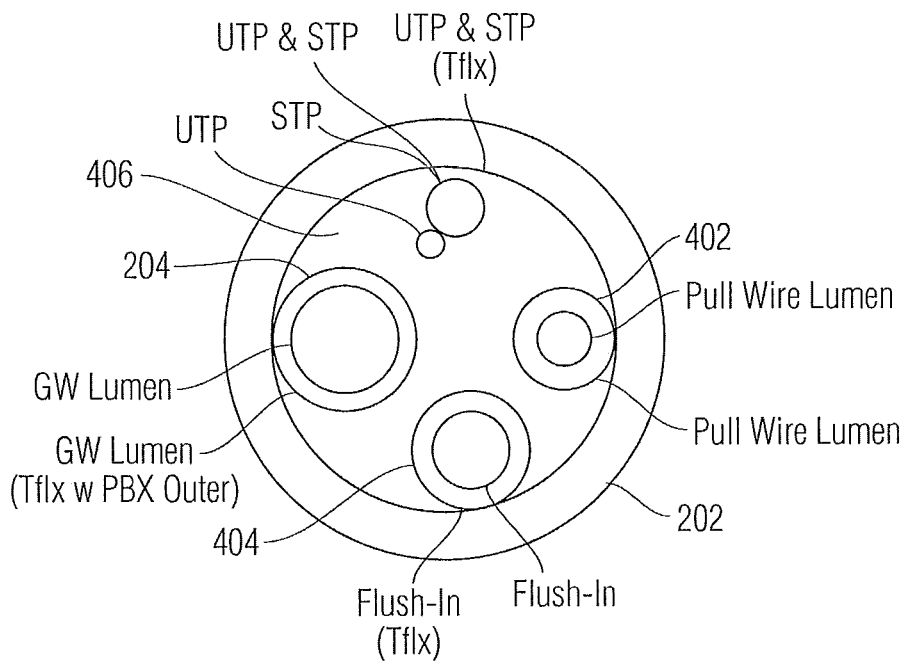
FIG. 4B is a variant cross-section view the delivery catheter of FIG. 2.

FIG. 4A illustrates an interior portion of the delivery catheter 202 in which several lumens are located. An acoustic transducer lumen 400 provides a conduit for the electrical wire that is used to actuate a shape memory alloy (SMA) that causes the transducer 206 to move in its sweep path, according to one embodiment of the invention. The acoustic transducer lumen 400 also provides a conduit for the electrical data wire that transmits the signals produced by the transducer 206 to the proximal end of the delivery catheter 202. The acoustic transducer lumen is optional and the electrical and data wires can be disposed in the interior lumen 406 of the catheter 202, as shown in FIG. 4B.

A steering wire lumen 402 provides a conduit for a steering wire that can be a pull wire or a push/pull wire that provides steering control for the distal end 201 of the tool 200. The steering wire is anchored to either the carriage 208 or otherwise in a distal portion of the catheter 202. Pushing or pulling the steering wire causes movement of the distal end 201 of the tool 200. This allows the user to simultaneously manipulate the acoustic transducer 206 and the medical device conduit 204 because the medical device conduit is mounted in parallel to the axis of the carriage 208. The steering wire permits the user to aim the acoustic transducer 206 and, therefore, a distal opening 205 opening of the medical device conduit 204 towards target tissue so that the user can visualize the target tissue and direct the opening 205 towards the visualized, target tissue for delivery of a medical device and/or other therapeutic agent to the target tissue. A steering mechanism (e.g. a handle) can impart both of the pulling and pushing forces (e.g., via a thumbwheel or slide connected to the proximal end of the steering wire(s)). Manipulating a steering wire to deflect the catheter 202 provides for macro-adjustment of the catheter 202, the transducer 206, and the opening 205 together. It is also possible to micro-adjust the conduit 204 and opening 205 via a separate conduit steering mechanism, as discussed below in connection with FIG. 7, for example.

Optionally, a flush lumen 404 is located within the delivery catheter 202. The flush lumen 404, when provided, provides a conduit for the delivery of saline or other suitable fluid to the cavity 216 between the acoustic transducer 206 and the acoustic window 210. A user injects saline into the flush lumen 404 at the proximal end of the flush lumen. The interior space 406 of the deliver catheter 202 that is not occupied by other lumens provides a return for the saline flush. Optionally, a separate lumen can be provided as a return for the flush. As the user continues to inject saline into the flush lumen 404, cavity 216 fills with saline and injection of saline is continued until saline fills the interior space 406 of the delivery conduit 204 such that saline exits the proximal end of the delivery catheter 202. This provides a fluid environment around the transducer 206 so as to minimize the effect of any boundary conditions, as noted above. Alternatively, a valve, such as a one-way valve or a two-way valve (similar to a valve of a Groshong catheter, for example), can be provided in the fluid flush path that maintains the fluid in the tip and surrounding the transducer 206, which avoids the need to inject saline until it exits out the proximal end of the delivery catheter 202 because the fluid is maintained locally in the tip region. This can provide more space efficiency in the delivery catheter 202. A port for injection of the fluid flush can optionally be provided in the side of the carriage or the distal end of the delivery catheter 202. This arrangement eliminates the need for a flush lumen to run from the distal end to the proximal end of the delivery catheter 202. The cavity 216 can also be pre-vacuumed and then saline is introduced into the cavity 216. Introducing the saline into a vacuumed cavity eliminates air bubbles and aids in the filling of the cavity with saline without the need for a return flush.

The medical device conduit 204 is disposed within the delivery catheter along a portion of the deliver catheter 202 that is proximate the carriage 208. The medical device conduit 204 provides a conduit for delivery of a medical device, for example, a guide wire, with at least one lumen that is fluidly separated from any saline or other fluid in the lumen of the delivery catheter 202. As can be seen in FIG. 2, the medical device conduit 204 transitions from the interior of the delivery catheter 202 to the exterior just proximal to the carriage 208.

FIGS. 5A and 5B provide a detailed view of the transition of the medical device conduit 204 from the interior to the exterior of the deliver catheter 202. In one embodiment, the delivery catheter 202 is made from PEBAX and includes an embedded braid 502. The delivery catheter 202 can be formed of other medically compliant, flexible materials used to make catheters and can include a coil rather than a braid. In an embodiment, the medical device conduit 204 is also PEBAX and includes an embedded coil 504. The medical device conduit 204 can be formed of other medically compliant, flexible materials used to make catheters and can include a braid rather than a coil. The medical device conduit 204 transitions from the interior to the exterior of the delivery catheter 202 in three transition zones 506, 508, and 510. In the first transition zone 506, the braid 502 of the delivery catheter 202 is generally intact and the medical device conduit 204 is disposed under the braid. In the second transition zone 508, the medical device conduit 204 passes between and through the braids 502 of the delivery catheter 202 without the need to sever the braids. However, depending on the braid angle and weave pattern, the braids can be severed to assist the medical device conduit 204 to pass through the braids 502. In the third transition zone 510, the medical device conduit 204 is located on the exterior side of the braid 502 of the delivery catheter 202. Through these three zones, the medical device conduit 204 transitions from an interior to an exterior of the delivery catheter 202 at a gradual angle so there are no tight bends in the medical device conduit. The delivery catheter 202 and the medical device conduit 204 can be heated together until the PEBAX of the delivery catheter 202 and the PEBAX of the medical device conduit 204 fuse together. The fusing of the two catheter and the conduit results in a fluid tight seal between the two catheters. This is accomplished without the need to use adhesive or other sealants. Adhesives or sealants can be used in addition to or as an alternative to the fusing of the catheter and conduit to provide a fluid tight seal. Providing the fluid tight seal maintains any saline within the interior of the delivery catheter 202 and prevents the saline from escaping into the patient. An optional jacket 512 is placed around the medical device conduit 204, the carriage 208, and a distal end portion of the delivery catheter 202. The jacket 512, which can be a polyethylene or other suitable material shrink wrap, secures the medical device conduit 204 adjacent the carriage 208 and runs parallel to the carriage 208 and the delivery catheter 202.

Figure 1C:
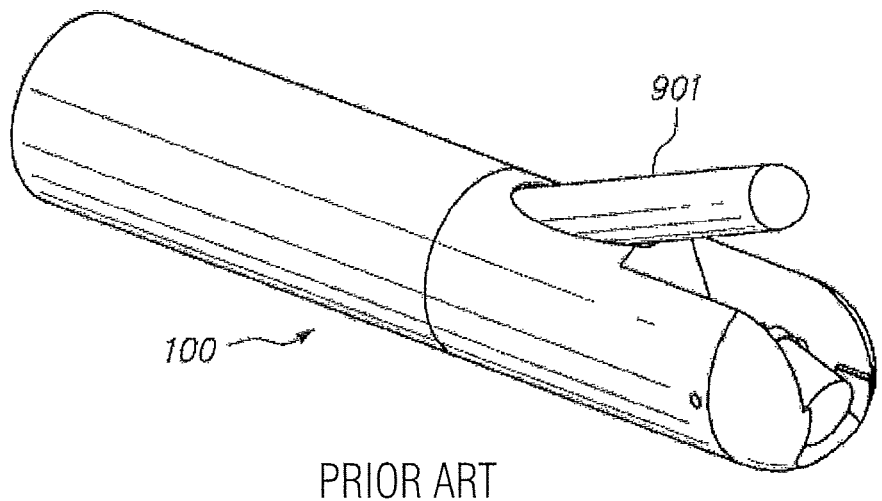
FIG. 1C is a perspective view of a forward-looking ultrasonic imaging device according to prior art.
Figure 1D:
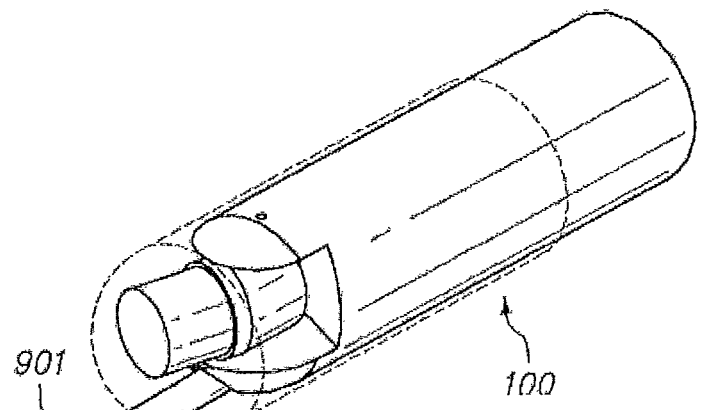
FIG. 1D is a partial cut-away perspective view of a forward-looking ultrasonic imaging device according to prior art.
Figure 1E:
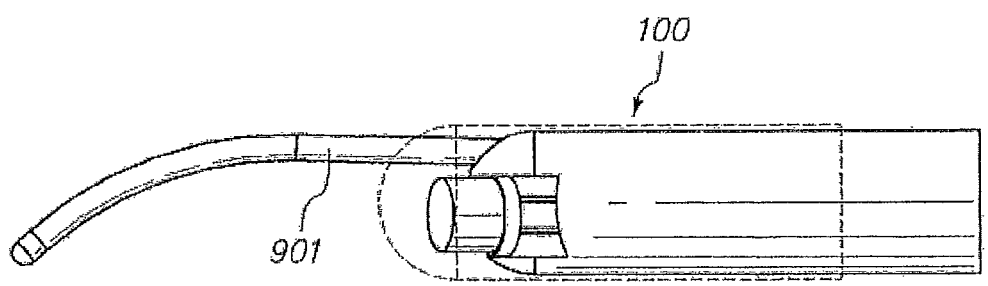
FIG. 1E is a partial cut-away side view of a forward-looking ultrasonic imaging device according to prior art.

Transitioning the medical device conduit 204 through the sidewall of the delivery catheter 202 provides the advantage that transition is very gradual, which eliminates sharp bends in the medical device conduit 204 that can impede the delivery of a medical device through the conduit 204. The prior art device shown in FIGS. 1C-1E, by contrast, shows a medical device 900 that is transitioned through the ultrasonic transducer carriage. This arrangement has several significant drawbacks. As can be seen in FIG. 1C, the transition through the carriage is relatively sharp, and so deployment of an instrument through this sharp bend can be difficult and reduce any tactile response that the clinician otherwise may have as a result of contacting tissue after advancing an instrument through the carriage. The transition cannot be made more gradual without extending the length of the carriage because a more gradual transition requires a gently angled hole. As can be seen in FIG. 1C, a more gently angled hole in the carriage would require a longer carriage in order to prevent the hole from interfering with the ultrasonic transducer. However, providing a longer carriage decreases the flexibility of the device because, unlike the flexible catheter materials in the arrangement of the present invention, the carriage itself is rigid. Thus, a longer carriage increases the difficulty to deploy the device through tortuous passages for percutaneous operations. In addition, passing a medical device through the carriage may interfere, abrade, or otherwise conflict with the and other elements that drive the ultrasonic transducer.

Figure 6:
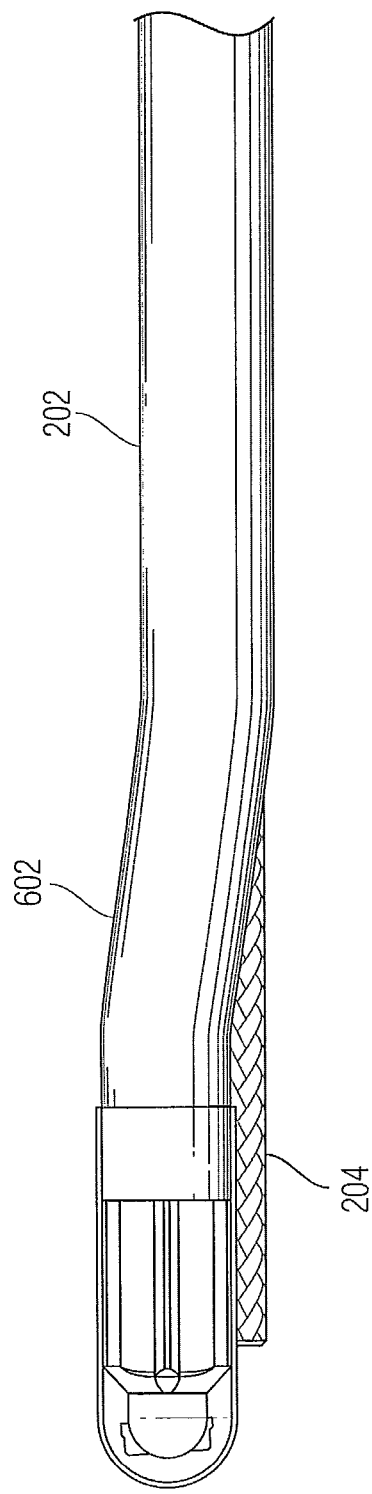
FIG. 6 is a side view of a delivery catheter with forward-looking ultrasound imaging device according to an embodiment of the invention.

As shown in FIG. 2, the medical device conduit 204 has a slight bend 207 as it transitions from the interior to the exterior of the delivery catheter 202. In an alternative embodiment, as shown in FIG. 6, the medical device conduit 204 remains straight as it transitions from the interior to the exterior of the delivery catheter 202, and it is the delivery catheter 202 that has a bend 602. This arrangement provides advantages by providing a medical device conduit 204 that is straight and avoids any impediments to deploying medical devices through a torturous path. It also maximizes the ability to push a medical device through the medical device conduit 204 without kinking. Meanwhile, by having the active mechanism for pivoting the transducer 206 co-located within the carriage 208 with the transducer, the delivery catheter 202 can accommodate the bend 602 without imparting a torque that otherwise could result from a remote coupling to a motive force at the catheter proximal end.

Figure 7A:
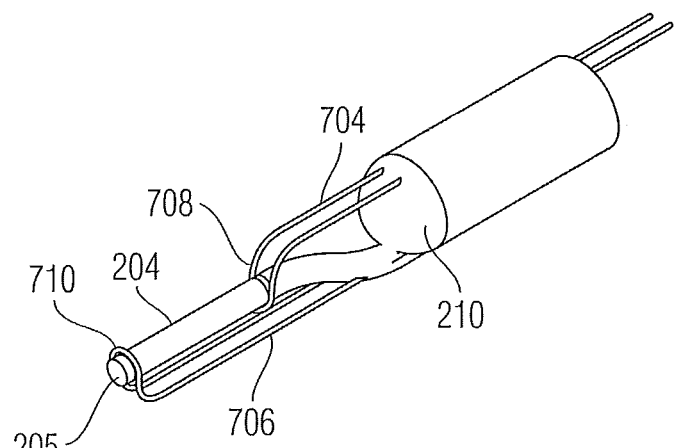
FIG. 7A is a perspective view of an end of a delivery catheter with forward-looking ultrasound imaging device according to an embodiment of the invention.
Figure 7B:
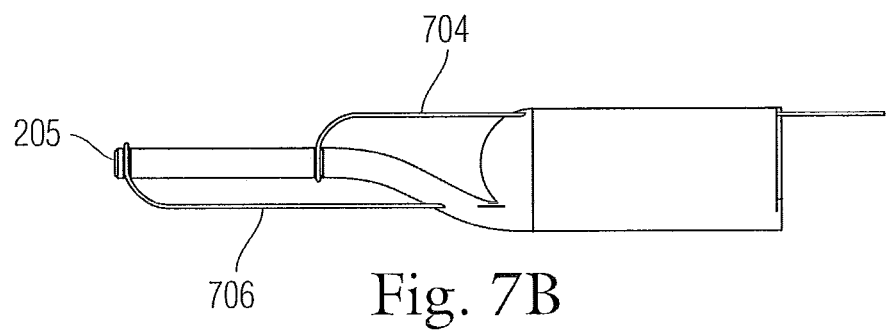
FIG. 7B is a side view of an end of a delivery catheter with forward-looking ultrasound imaging device according to an embodiment of the invention.
Figure 7C:
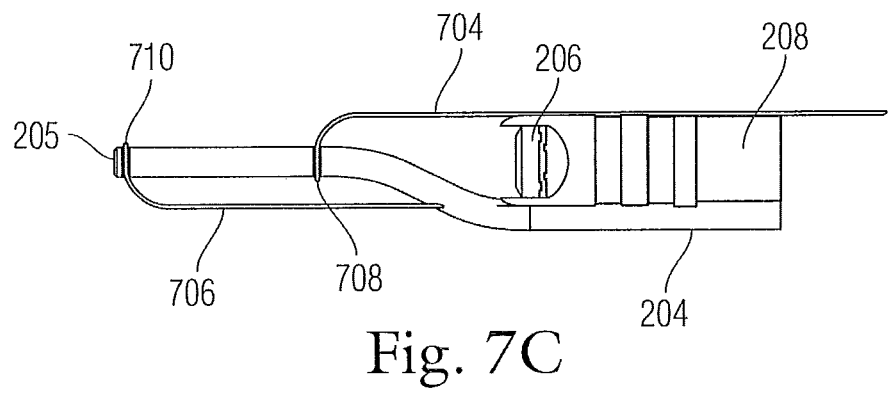
FIG. 7C is a partial cut-away side view of an end of a delivery catheter with forward-looking ultrasound imaging device according to an embodiment of the invention.

In the embodiment illustrated in FIGS. 7A, 7B, and 7C, the medical device conduit 204 includes a distal extension portion that extends distally beyond the acoustic window 210. This arrangement is advantageous because it defines a space between any tissue abutting the distal extension and the ultrasonic transducer 206 which provides for optimal imaging of the target tissue while concurrently supporting a medical device, via the extension portion of the medical device conduit 204, beyond the transducer 206 itself. Maintaining the transducer 206 at a distance, for example, 10 to 25 mm, from the target tissue provides a larger imaging field of view. When the transducer is directly adjacent to the target tissue, the field of view is narrow and limited to a very small area. A narrow field of view is not desirable because it is difficult to perceive the location of the transducer and medical device conduit because the narrow field of view precludes visualization of anatomical landmarks in the patient. Providing the extension portion, however, provides a mechanism to ensure spacing of the transducer 206 from the target tissue while also allowing the opening 205 to be placed directly adjacent the target tissue.

Support struts 704 and 706 support the extension portion of the conduit 204 and maintain the device conduit 204 in a desired position relative to the transducer 206. The support struts 704 and 706 maintain the extension portion of the conduit 204 concentrically located with the carriage 208 and in the field of view of the transducer 206. As the transducer 206 sweeps back and forth during its operation, the position of the extension and the surrounding tissue is visualized. Accordingly, the position of the opening 205 through which a medical device is delivered (e.g., a guide wire) can be visualized so that a user can ensure accurate deployment of the medical device. The struts 704 and 706 are preferably a thin, flexible material, such as nitinol or laser cut from a hypotube, for example, so that they provide support to the extension portion of the conduit 204 while also being flexible enough to be deployed through a guide sheath into the heart without risk of tissue perforation. The struts 704 and 706 are formed with collar portions 708 and 710 that seat the extension portion of conduit 204. Alternatively, the struts can be looped around the extension portion such that the conduit 204 is seated in the loops formed by the struts. The collars portions 708 and 710 can also be at least partially fused into the material of the sidewall (e.g., PEBAX) of the medical device conduit 204. As can be seen in FIG. 3, the carriage 208 can be formed with grooves 218 to seat the struts 704 and 706 to assist in anchoring the struts. FIG. 7 illustrate just one example of a strut arrangement, and other structural arrangements of struts can be used to support the conduit extension. For example, the struts can be coupled to single collar, the struts can each be a single wire construction, and a plurality of struts can be used and arranged in different positions depending on the anatomical structures and desired performance characteristics required for a particular medical procedure. In a variation, the proximal ends of the struts 704 and 706 extend proximally into the interior of the delivery catheter 202 and to the proximal end of the catheter (not shown). Imparting compression and/or tension force on the proximal ends of the struts causes a deflection at their distal ends. The deflection at the distal ends of the struts can be used for micro-adjustment of the extension portion of the medical device conduit 204. Adjusting the extension portion of the medical device conduit 204 allows the user to direct the opening 205 of the conduit 204 without adjusting the position of the delivery catheter 202.

Accordingly, an instrument can be advanced independently of the positioning of the delivery catheter within an isolated lumen of the medical device conduit 204, and thereafter the exit angle of the medical deliver catheter can be micro-adjusted. This can be done without adjusting the field of view of the transducer, if desired. Accordingly, manipulating a steering wire anchored to the carriage 208, for example, provides for macro-adjustment of the distal end of the catheter 202, the transducer 206, and the medical device conduit 204 while manipulation of the struts provides for micro-adjustment of the conduit 204 without repositioning or dislodging the catheter 202. In one arrangement, imparting a compressive force on strut 706 causes the opening 205 to bend in a direction toward strut 704, and imparting a tensile force on strut 706 causes the opening 205 to bend in a direction away from strut 704. Applying force to one of the two wires of a strut while keeping the other wire fixed or applying an opposite force to the other wire can be used to cause deflection in a direction that is in or out of the image plane of FIG. 7B. A steering mechanism can impart both of these tensile and compressive forces at the same time (e.g., via a thumbwheel or slide connected to the proximal end of the struts).

In one example of use, a guide wire is passed through the mitral annulus of the heart using the tool 200. The distal opening 205 of the medical device conduit 204 is positioned adjacent a ventricular side of the mitral annulus. The position of the distal opening is confirmed via the transducer 206 to ensure proper placement of the guide wire. Optionally, the distal opening 205 is positioned distal to the transducer 206 and spaced therefrom by the length of the struts so as to better ensure an optimal field of view for a mitral annulus procedure, namely, a spacing of about 10 mm from the tissue to provide ultrasound images that include the region between the transducer and the distal opening, as well as a view into the tissue itself to a depth of about 15 mm. The guide wire is inserted into the proximal end of the medical device conduit 204. The wire is advanced toward the distal end of the delivery catheter 202 as the device conduit 204 transitions from an interior to an exterior of the delivery catheter 202. The guide wire is further advanced into the extension portion of the device conduit 204, when such an extension is provided. As the user advances the guide wire through the mitral annulus to the atrial side, the struts 704 and 706 of the extension portion maintain the position of the conduit 204 and the transducer 206 provides visualization of the positioning of the guide wire deployment. The struts 704 and 706 and the extension portion of the conduit 204 also provide support to the guide wire (or other medical device) as it manipulated and advanced. The extension portion of the conduit 204 further provides a structural guide as it is abutted against the target tissue that automatically maintains the imaging transducer an optimal distance from the target tissue for viewing.

Figure 8A:
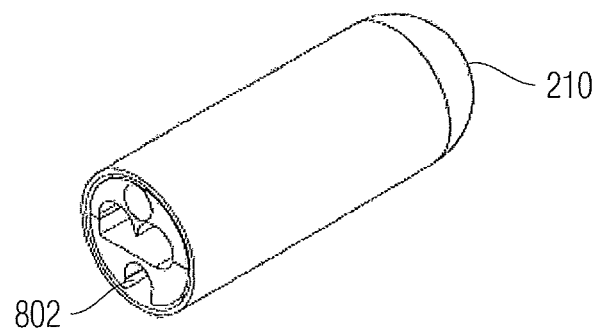
FIG. 8A is a perspective view of an end of a delivery catheter with forward-looking ultrasound imaging device according to an embodiment of the invention.
Figure 8B:
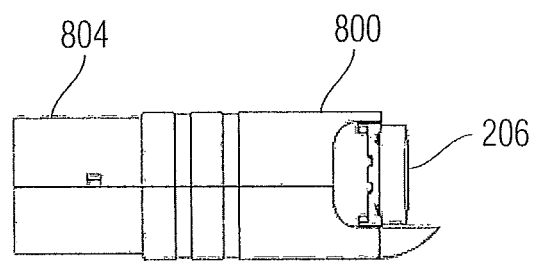
FIG. 8B is a partial cut-away side view of an end of a delivery catheter with forward-looking ultrasound imaging device according to an embodiment of the invention.
Figure 8C:
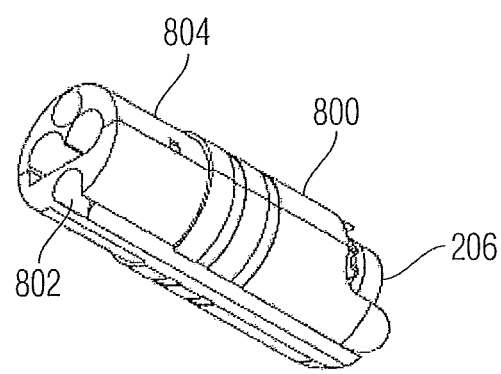
FIG. 8C is a partial cut-away perspective view of an end of a delivery catheter with forward-looking ultrasound imaging device according to an embodiment of the invention.

In the embodiments shown in FIGS. 2, 5, 6, and 7, the medical device conduit 204 transitions from an interior to an exterior of the delivery catheter 202 and is disposed alongside the carriage 208. In these embodiments, the device conduit 204 exits the delivery catheter 202 in order to go around and extend past the carriage 208. In one embodiment as shown in FIG. 8, a carriage 800 is provided with a trough 802 that seats the device conduit 204. The trough 802 and the conduit 204 can be sized so that when the conduit is seated in the trough a fluid seal is formed. The device conduit 204 is seated in the trough 802 and then the delivery catheter is seated over the shoulder 804 of the carriage 800 and over the medical device conduit 204 with the device conduit disposed on the interior of the delivery catheter 202. The medical device conduit 204 extends within the delivery catheter to a proximal end of the delivery catheter and, as such, can isolate any device within the delivery catheter from wires, fluids, and elements within the delivery catheter. The trough 802 allows the medical device conduit 204 to remain inside the interior of the delivery catheter 202 and eliminates the transition of the medical device conduit from the interior to the exterior of the delivery catheter 202 through the sidewall of the delivery catheter 202. Therefore, there is no need to penetrate the sidewall of the catheter 202. This arrangement provides several advantages over the prior art arrangements because it eliminates the need for a bend in the medical device conduit.

The acoustic window 210 includes a hole (not shown) that is substantially aligned with the trough 802. The hole is sized to allow the medical device conduit 204 to seat in the hole. The sizing of the hole and the conduit can be such that seating of the medical device conduit 204 in the hole provides a fluid-tight seal. The seal prevents saline in the cavity 216 from escaping through the hole in the window. Adhesive can be applied to provide a fluid seal between the conduit 204 and the hole, in a variation of the foregoing. Additionally or alternatively, the materials of the conduit 204 and the window can be fused to provide sealing.

The medical device conduit 204 can terminate substantially flush with the acoustic window 210 or extend distally past the window 210. This structural arrangement permits a medical device (e.g., guide wire, needle, etc.) to be deployed past the distal end of the acoustic window 210 and in the field of view of the transducer 206 for visualization of the medical device and the target tissue. In a further arrangement, the medical device conduit 204 has an extension to space its distal opening 205 ahead of the transducer window by a prescribed amount. The extension can include struts for support, as previously described. Preferably, the medical device conduit exits the carriage at a location that minimally interferes with the field of view provided by movement of the transducer 206.

The invention and embodiments described herein can be used for a number of different surgical procedures and applications. For example, the device can provide direct visualization the transducer and delivery of needles and guide wire delivery systems through the conduit 204. The device can be used for, among other procedures, mitral annulus penetration; transseptal procedures; arterial puncture; fine needle aspiration of the lungs; fine needle aspiration in gastrointestinal procedures; fine needle aspiration of the uterus, ovaries, etc. in genitourinary procedures. Other applications that can benefit from the use of the device include structural heart repair; valve repair; valve replacement; perivalvular leak closure; patent foramen ovale (PFO) closure; atrial septal defect (ASD) closure; ventricular septal defect (VSD) closure; transseptal needle delivery; left atrial appendage closure; electrode delivery; coil delivery; stem cell delivery; biologics delivery; tissue injection; vascular access & closure (e.g. femoral artery for cardiovascular procedure); vascular access catheter placement to optimize position for flow and to minimize turbulence/thrombus formation (e.g. dialysis catheter or PICC line); stent delivery; urinary tract therapy (e.g. kidney stones, incontinence implants); artificial insemination; vascular blockage (e.g. stroke); brain therapy (e.g. tumor); pain management; cerebrospinal access and closure; lymph system therapy (navigation of lymph ducts); gastrointestinal therapy; hepatic therapy; pancreatic therapy; natural orifice translumenal endoscopic surgery (NOTES) (e.g. access, closure, diagnostics, and therapy delivery, etc.); aortic and thoracic aneurism therapy (e.g. tissue assessment for stent anchor placement, peri-stent leakage, etc); renal artery access; tissue biopsy; musculoskeletal procedures (e.g. joint therapy); and ENT (Ear nose and throat) therapy, energy based therapy (e.g. cryogenic, infrared, radio frequency), for example. These are just a few of the procedures and applications in which the device may be used and are non-limiting examples.

While the invention has been described in connection with certain embodiments thereof, the invention is not limited to the described embodiments but rather is more broadly defined by the features recited in the claims below and equivalents of such features.

The invention claimed is:

1. A catheter based medical device for a percutaneous surgical procedure that provides forward-looking visualization and is configured to deliver a medical device, comprising:
   a catheter having a distal end, a proximal end, and a sidewall defining an interior lumen;
   a carriage supported by the distal end of the catheter;
   an ultrasonic transducer supported by the carriage such that the transducer is free to move in a sweep path;
   a conduit having a proximal end, a distal end, and a sidewall defining a second interior lumen, the proximal end of the conduit being disposed within the interior lumen of the catheter such that a length of the conduit extends longitudinally within the interior lumen, wherein the conduit passes through the sidewall of the catheter at a location spaced from the distal end of the catheter such that a first portion of the conduit extends longitudinally along an exterior of the sidewall of the catheter, with the distal end of the conduit being disposed external to the sidewall of the catheter, wherein a longitudinal axis of the first portion of the conduit is parallel to a longitudinal axis of the catheter; and
   wherein the conduit is configured for receiving a medical device through the second interior lumen of the conduit and wherein the ultrasonic transducer permits visualization of the medical device distally of the transducer.

2. A catheter based medical device according to claim 1, wherein the sidewall of the conduit is in contact with the sidewall of the catheter at the location at which the conduit passes through the sidewall of the catheter.

3. A catheter based medical device according to claim 1, wherein the first portion of the conduit extends longitudinally along an exterior surface of the carriage.

4. A catheter based medical device according to claim 1, wherein the catheter includes a transition region at which the conduit passes through the sidewall of the catheter, the transition region being at least partially defined by a braided material and being defined by first, second and third transition regions.

5. A catheter based medical device according to claim 4, wherein in the first transition region, the braided material of the catheter is intact and the conduit is disposed under the braids of the braided material; wherein in the second transition region, the conduit passes between and through the braids of the catheter without severing the braids; and wherein in the third transition region, the conduit is disposed entirely along the exterior of the sidewall of the catheter.

6. A catheter based medical device according to claim 1, wherein the first portion of the conduit is connected to the exterior of the sidewall of the catheter, thereby providing a fluid seal between the conduit and the catheter.

7. A catheter based medical device according to claim 1, wherein the location at which the conduit passes through the sidewall of the catheter is located proximate to the carriage.

8. A catheter based medical device according to claim 1, further including a jacket that is disposed around: (1) at least a length of the conduit; (2) at least a length of the catheter; and (3) at least a length of the carriage.

9. A catheter based medical device according to claim 8, wherein the jacket is formed of a shrink wrap material.

10. A catheter based medical device according to claim 1, wherein a distal end portion in the form of an extension of the conduit extends distal to a distal end of the carriage and at least one elongated strut support the distal end portion.

11. A catheter based medical device according to claim 10, wherein the strut support includes a loop section that encircles the distal end portion.

12. A catheter based medical device according to claim 1, wherein the catheter comprises an embedded braid structure.

13. A catheter based medical device according to claim 1, wherein the distal end of the conduit is located adjacent the ultrasonic transducer.

14. A catheter system for use in a percutaneous surgical procedure comprising:
  a catheter having a distal end, a proximal end, and a sidewall defining an interior lumen;
  a carriage supported by the distal end of the catheter;
  an ultrasonic transducer supported by the carriage such that the transducer is free to move in a sweep path;
  a conduit having a proximal end, a distal end, and a sidewall defining a second interior lumen, the proximal end of the conduit being disposed within the interior lumen of the catheter such that a length of the conduit extends longitudinally within the interior lumen, wherein the conduit passes through the sidewall of the catheter at a location spaced from the distal end of the catheter such that a first portion of the conduit extends longitudinally along an exterior of the sidewalk of the catheter, with the distal end of the conduit being disposed external to the sidewall of the catheter, wherein a longitudinal axis of the first portion of the conduit is parallel to a longitudinal axis of the catheter; and
  a medical device that is configured to pass through the second interior lumen of the conduit for delivery to a surgical site and wherein the ultrasonic transducer is configured to permits visualization of the medical device distally of the transducer.

15. A catheter system for use in a percutaneous surgical procedure comprising:
  a catheter having a distal end, a proximal end, and a sidewall defining an interior lumen;
  a carriage supported by the distal end of the catheter;
  an ultrasonic transducer supported by the carriage such that the transducer is free to move in a sweep path;
  a conduit in the form of a tubular structure having a proximal end, a distal end, and a sidewall defining a second interior lumen, the proximal end of the conduit being disposed within the interior lumen of the catheter that is defined by the sidewall of the catheter such that a length of the conduit extends longitudinally within the interior lumen, wherein the conduit passes through the sidewall of the catheter at a location spaced from the distal end of the catheter such that a first portion of the conduit extends longitudinally along an exterior of the sidewall of the catheter, with the distal end of the conduit being disposed external to the sidewall of the catheter, wherein a longitudinal axis of the first portion of the conduit is parallel to a longitudinal axis of the catheter; and
  a medical device that is configured to pass through the second interior lumen of the conduit for delivery to a surgical site and wherein the ultrasonic transducer is configured to permits visualization of the medical device distally of the transducer;
  wherein the catheter includes a transition region at which the conduit passes through the sidewall of the catheter, the transition region being at least partially defined by a braided material and being defined by first, second and third transition regions, wherein in the first transition region, the braided material of the catheter is intact and the conduit is disposed under braids of the braided material and lies entirely within the interior lumen of the catheter; wherein in the second transition region, the conduit passes physically between and through the braids of the catheter without severing the braids; and wherein in the third transition region, the conduit is disposed entirely along the exterior of the sidewall of the catheter; and wherein the conduit is formed of a braided material.

* * * * *